United States Patent
Xie

(10) Patent No.: US 12,337,100 B2
(45) Date of Patent: Jun. 24, 2025

(54) ASSEMBLY OF CARTRIDGE AND FLAT HEAT ELEMENT FOR MICROVAPORIZER

(71) Applicant: CENTRAL VICTORY LIMITED HK, Hong Kong (CN)

(72) Inventor: Haojun Xie, Guangxi (CN)

(73) Assignees: Donovan Phillips, Richmond, VA (US); James Xu, Richmond, VA (US)

( * ) Notice: Subject to any disclaimer, the term of this patent is extended or adjusted under 35 U.S.C. 154(b) by 908 days.

(21) Appl. No.: 17/431,587

(22) PCT Filed: May 6, 2019

(86) PCT No.: PCT/CN2019/085706
§ 371 (c)(1),
(2) Date: Aug. 17, 2021

(87) PCT Pub. No.: WO2020/223875
PCT Pub. Date: Nov. 12, 2020

(65) Prior Publication Data
US 2022/0134025 A1  May 5, 2022

(51) Int. Cl.
| | |
|---|---|
| *A24F 40/485* | (2020.01) |
| *A24F 7/02* | (2006.01) |
| *A24F 40/10* | (2020.01) |
| *A24F 40/42* | (2020.01) |
| *A24F 40/46* | (2020.01) |

(Continued)

(52) U.S. Cl.
CPC ............ *A61M 11/042* (2014.02); *A24F 7/02* (2013.01); *A24F 40/10* (2020.01); *A24F 40/42* (2020.01); *A24F 40/46* (2020.01); *A24F 40/485* (2020.01); *A61M 15/06* (2013.01); *H05B 3/06* (2013.01); *H05B 3/286* (2013.01); *A61M 2205/3653* (2013.01); *H05B 2203/021* (2013.01)

(58) Field of Classification Search
CPC ..... A61M 11/042; A61M 15/06; A24F 40/10; A24F 40/42; A24F 40/46; A24F 40/30; A24F 40/40
See application file for complete search history.

(56) References Cited

U.S. PATENT DOCUMENTS 10,765,147 B2 *  9/2020  Buchberger .......... A61M 15/06
11,317,652 B2 *  5/2022  Watanabe ............. A61M 15/06
(Continued)

FOREIGN PATENT DOCUMENTS

CN       1541577       11/2004
CN     206079043        4/2017
(Continued)

OTHER PUBLICATIONS

International Search Report for PCT/CN2019/085706, mailed Feb. 19, 2020, 6 pages.
(Continued)

*Primary Examiner* — Timothy A Stanis
*Assistant Examiner* — Sara K Toich
(74) *Attorney, Agent, or Firm* — Nixon & Vanderhye P.C.

(57) ABSTRACT

A microvaporizer (10) including a cartridge (14), a flat plate heater (16) and a base (12). The cartridge (14) includes a mouth piece (40) configured to deliver an aerosol to the user's airways. The cartridge (14) also includes a hollow main body (42) with a recessed wall (60) to receive the flat plate heater (16).

16 Claims, 7 Drawing Sheets

(51) Int. Cl.
    *A61M 11/04*     (2006.01)
    *A61M 15/06*     (2006.01)
    *H05B 3/06*     (2006.01)
    *H05B 3/28*     (2006.01)

(56) References Cited

U.S. PATENT DOCUMENTS

| | | | | |
|---|---|---|---|---|
| 2013/0333700 | A1* | 12/2013 | Buchberger | A61M 16/1075 128/203.26 |
| 2014/0286630 | A1* | 9/2014 | Buchberger | A61M 11/041 392/395 |
| 2015/0216237 | A1* | 8/2015 | Wensley | A24F 40/48 131/273 |
| 2016/0262454 | A1* | 9/2016 | Sears | B01F 23/2133 |
| 2017/0006916 | A1 | 1/2017 | Liu | |
| 2017/0231283 | A1* | 8/2017 | Gadas | A24F 7/02 131/329 |
| 2017/0251727 | A1* | 9/2017 | Nielsen | A24F 40/40 |
| 2018/0070641 | A1* | 3/2018 | Batista | A24F 40/50 |
| 2018/0077967 | A1* | 3/2018 | Hatton | A24F 40/40 |
| 2018/0271150 | A1* | 9/2018 | Sparklin | A61M 15/025 |
| 2019/0142071 | A1* | 5/2019 | Seok | A24F 40/46 131/329 |
| 2019/0216135 | A1* | 7/2019 | Guo | A24F 40/44 |
| 2020/0163383 | A1* | 5/2020 | Kessler | H05B 3/265 |

FOREIGN PATENT DOCUMENTS

| | | |
|---|---|---|
| CN | 107713026 | 2/2018 |
| CN | 108514158 | 9/2018 |

OTHER PUBLICATIONS

Written Opinion of the ISA for PCT/CN2019/085706, mailed Feb. 19, 2020, 4 pages.

* cited by examiner

ASSEMBLY OF CARTRIDGE AND FLAT HEAT ELEMENT FOR MICROVAPORIZER

This application is the U.S. national phase of International Application No. PCT/CN2019/085706 filed 6 May 2019, which designated the U.S., the entire contents of which is hereby incorporated by reference.

TECHNICAL FIELD

The invention relates to microvaporizers, e.g., vaping devices, and particularly relates fluid containers and heaters for microvaporizers.

BACKGROUND ART

Microvaporizers (also referred to a vaping devices) are often used to dispense one or more active substances using the vaporized material. In atmospheric dispensers the substances may include materials such as deodorizing fragrance, medicine, nicotine, and insect repellent. In the case of personal vaporizers the active substances typically include a flavor and/or nicotine. The flavor and nicotine strength can be dialed up or down so as to mimic a traditional smoking experience. In general the vaporized material is the sole source of active substances in the micovaporizor.

Heaters in microvaporizers typically include a coiled heating wire wrapped around a wick or other fluid conduit that draws a liquid infused with chemicals (such as nicotine) from a reservoir. The coiled heating wire heats the liquid in the wick or received from the conduit. The liquid is vaporized by the heating. The vapor flows from the heating wire through a mouthpiece and to the user.

SUMMARY OF INVENTION

Technical Problem

The heating wire, devices to hold the wick, fluid passages from the reservoir and to the wick are typically complex in a conventional microvaporizer. The connections between the heating wire, wick and reservoir tend to require complex fittings and other connection related devices. These fittings and devices are often complex and costly to manufacture, and may be difficult to use.

There is a long felt need for a simple and easy to assemble heater, wick or related fluid conduit, and fluid reservoir.

Solution to Problem

Technical Solution

The inventors conceived of an assembly including a flat heater and cartridge which may be assembled together and then mounted in a base unit, which may be a handheld device. The cartridge may include a pathway for aerosol to reach the user, with an interface to connect to a device or mouthpiece. The cartridge may also include an internal fluid reservoir and a flat sided mount to receive the flat heater.

The mount may be a recess in the side of the cartridge having a flat bottom and configured to receive and hold the flat heater. An inlet port on the flat bottom may allow liquid from the internal reservoir in the cartridge to flow into fluid passages in the flat heater. A pump in the internal reservoir may pump liquid from the reservoir into the flat heater and towards heating elements in the heater.

An outer flat surface of the flat heater may be flush, e.g., in the same plane as, the side of the cartridge with the recess. The outer flat surface of the heater has an outlet, adjacent the heating elements, to allow vapor, e.g., an aerosol, generated by heating liquid flowing through the heater to flow from the cartridge and heater into a mouthpiece of the microvaporizer.

The cartridge and flat heater may be simple structures which may be manufactured at a low cost as compared to conventional liquid delivery systems in microvaporizers.

The cartridge may include a mouth piece configured to deliver an aerosol to the user's airways and a hollow main body with a recessed wall. The cartridge may also include a flat heater mounted to the recessed wall of the hollow main body.

The recessed wall may include two openings configured to fluidly connect to the fluid passages in the heater. At least one of the two openings may include a seal, and the seal may be an O-ring. One of the openings may be configured to fluidly connect to an inlet of the heater, and the other one of the openings may be configured to fluidly connect to an outlet of the heater.

The recessed wall may further include a mounting structure configured to engage the heater to align the heater within a recess in the hollow main body. The mounting structure may include a pair of protrusions configured to engage a respective pair of openings in the heater.

Another aspect of the technology may include a microvaporizer device configured to deliver an aerosol to a user's airways. The microvaporizer device may include a power supply and the cartridge described above.

Yet another aspect of the technology may include a cartridge configured to be mounted to a microvaporizer device. The cartridge may include a mouth piece configured to deliver an aerosol to the user's airways. The cartridge may also include a hollow main body with a recess and a storage tank configured to retain a chemically infused liquid. The storage tank may be contained inside the hollow main body. The cartridge may also include a flat heater removably mounted to a recessed wall in the recess of the hollow main body. The flat heater may be a unitary component configured so that positioning the heater in the recess fluidly connects the heater to the storage tank and the mouth piece.

The flat heater may be configured so that an outer surface of the heater is flush with an outer surface of the cartridge when the heater is positioned in the recess.

The heater may be configured to be retained in the recess by friction.

The cartridge may further include a pump configured to pump liquid in and out of the storage tank. In addition, the pump may be configured to pump liquid in and out of the heater.

The cartridge may further comprising a screw valve. In addition, the screw valve may include opposing gears.

Yet another aspect of the technology may include a microvaporizer device configured to deliver an aerosol to a user's airways. The microvaporizer device may include a power supply and the cartridge described above.

Yet another aspect of the technology may include a cartridge configured to be mounted to a microvaporizer device. The cartridge may include a mouth piece configured to deliver an aerosol to the user's airways and a hollow main body with a recessed planar wall that comprises a supply port and a discharge port. The cartridge may also include a flat heater removably mounted to the recessed wall. The flat heater may be configured so that an inlet of the flat heater aligns with the supply port and an outlet of the flat heater aligns with the discharge port when the flat heater is secured against the recessed planar wall.

The flat heater may be configured to be secured against the recessed planar wall by snapping the heater in place The cartridge may further include a storage tank configured to retain a chemically infused liquid. The storage tank may be contained inside the hollow main body and being fluidly connected to the supply port.

Yet another aspect of the technology may include a microvaporizer device configured to deliver an aerosol to a user's airways. The microvaporizer device may include a power supply and the cartridge described above.

Advantageous Effects of Invention

BRIEF DESCRIPTION OF DRAWINGS

Description of Drawings

Figure 1:
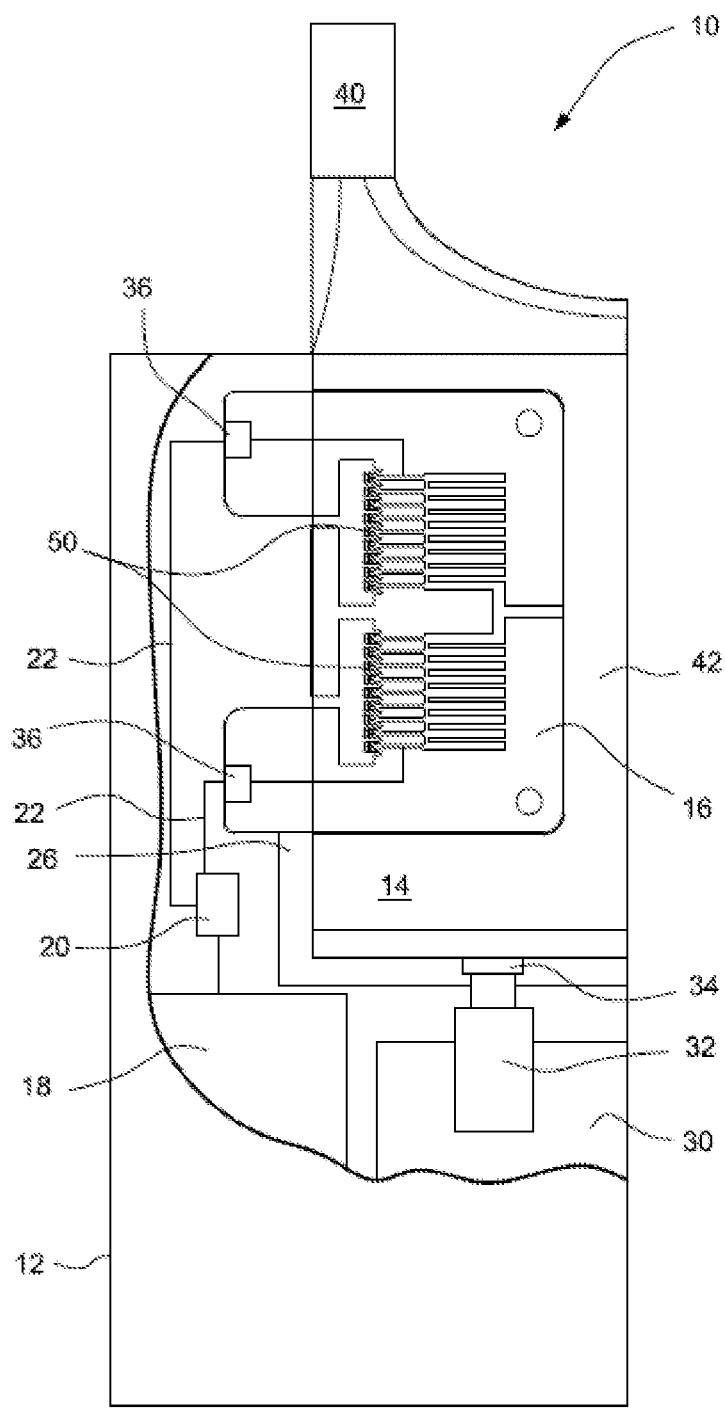

FIG. 1 shows an exemplary microvaporizer including a base, cartridge and heater, with a portion of a sidewall of the base removed to show the cartridge and heater.

Figure 2:
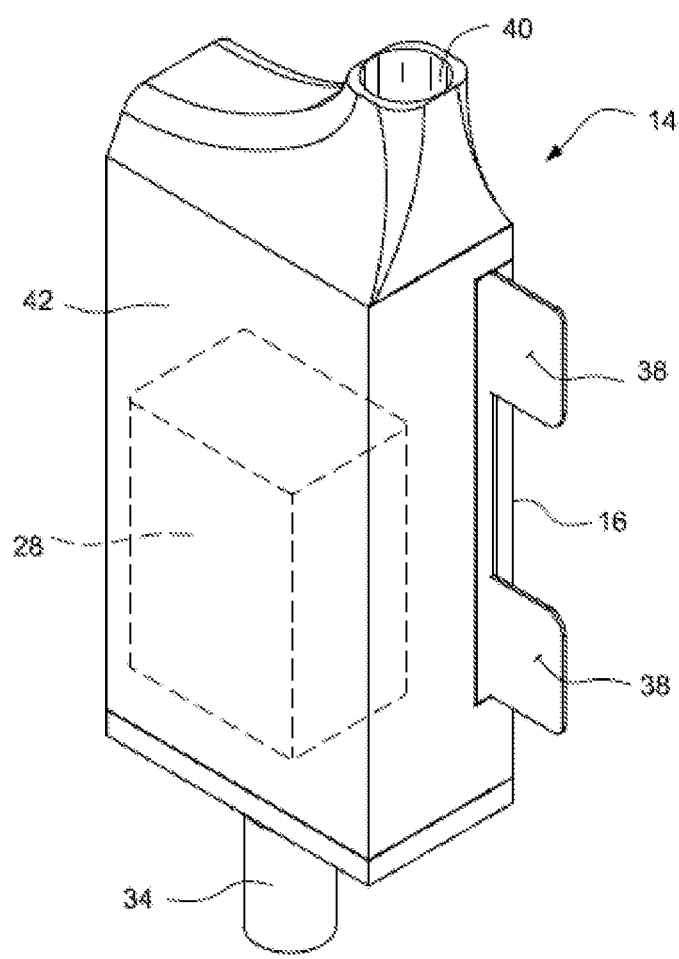

FIG. 2 is a perspective view of the cartridge and heater shown in FIG. 1.

Figure 3:
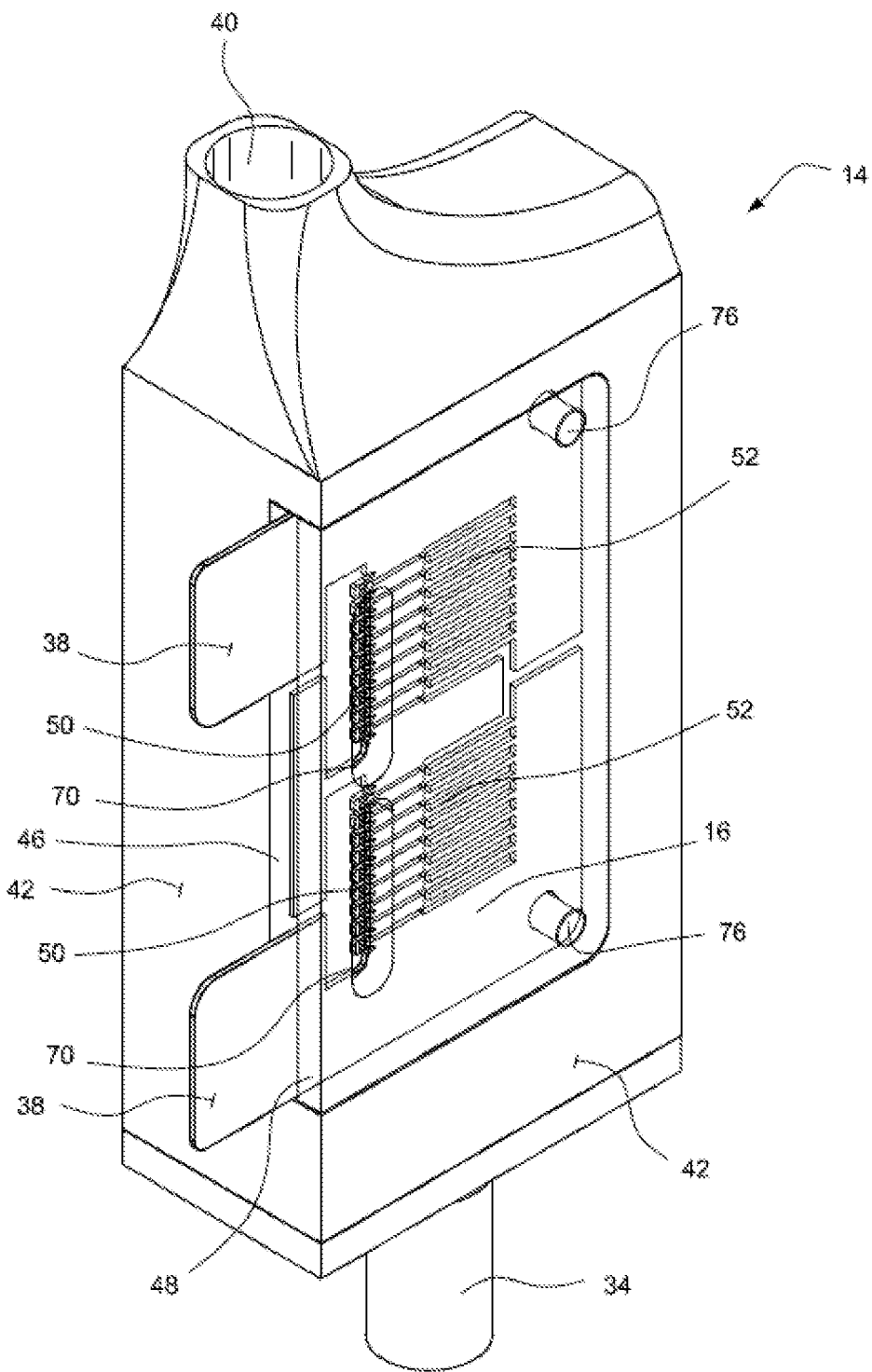

FIG. 3 is another perspective view of the cartridge and heater shown in FIG. 1.

Figure 4:
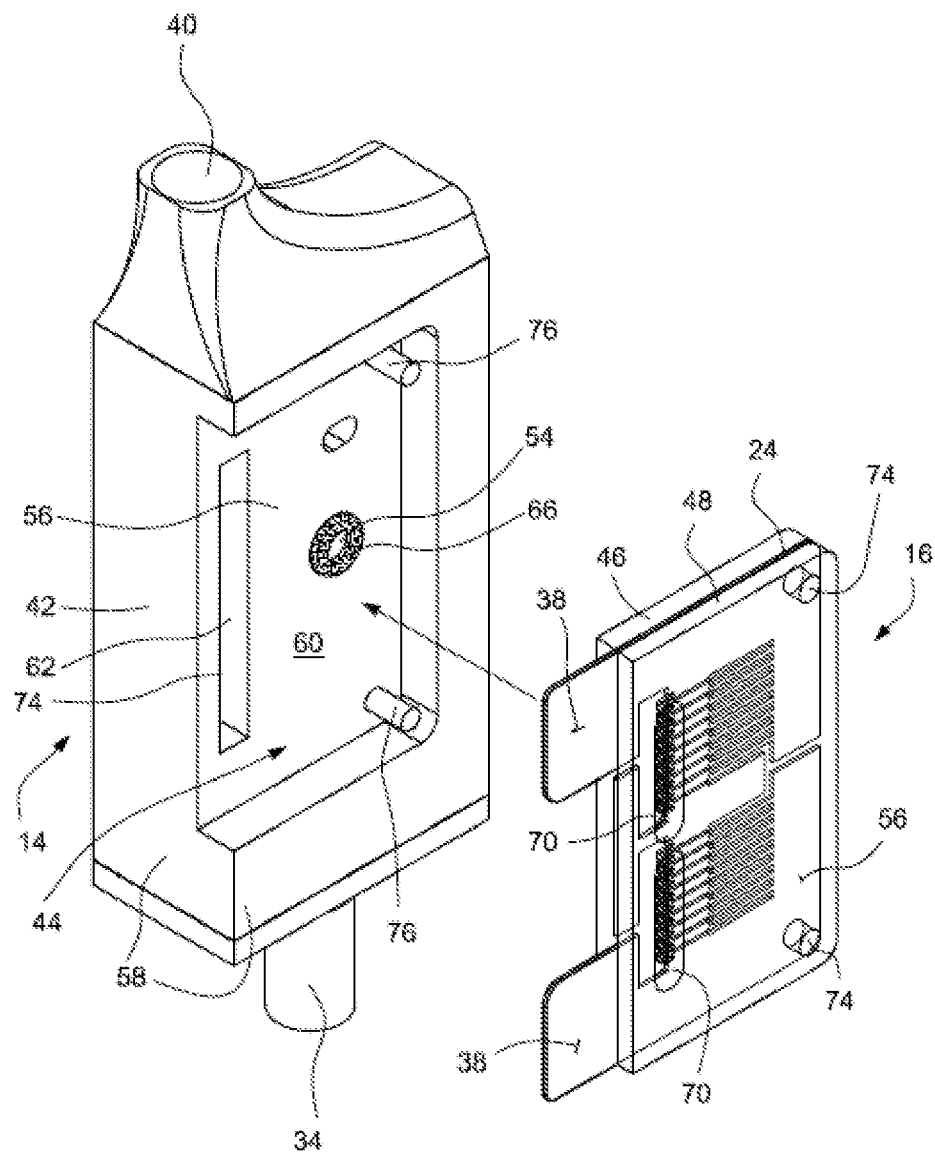

FIG. 4 is an exploded view of the cartridge and heater shown in FIG. 1.

Figure 5:
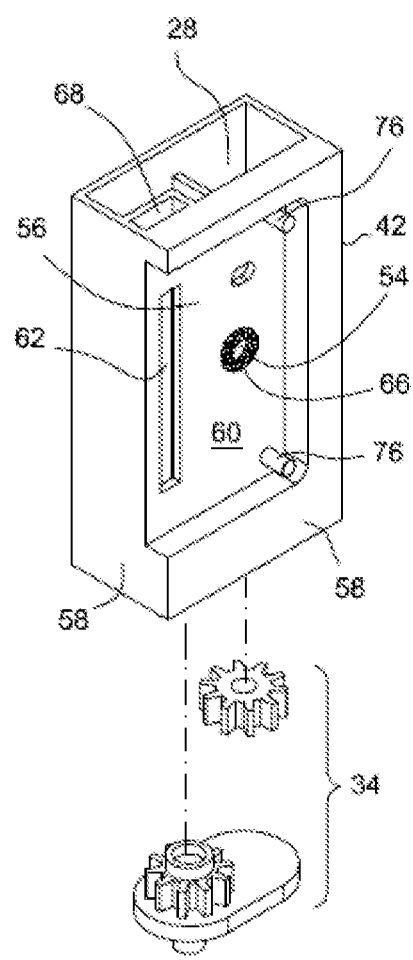

FIG. 5 is a perspective view of the hollow main body of the cartridge.

Figure 6:
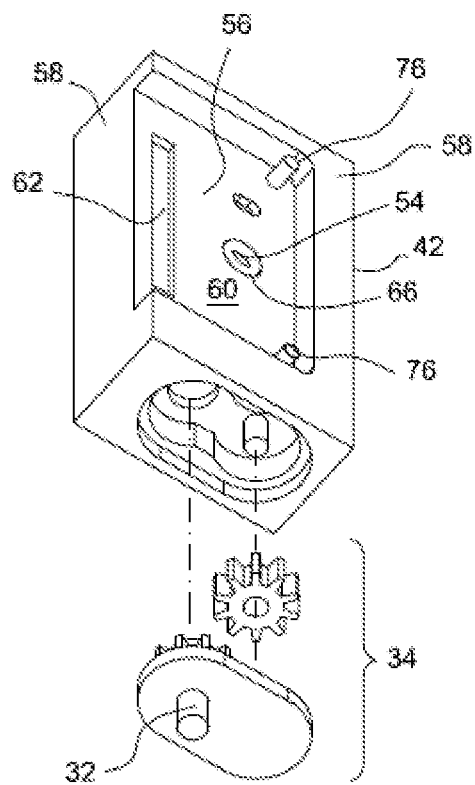

FIG. 6 is another perspective view of the hollow main body of the cartridge.

Figure 7:
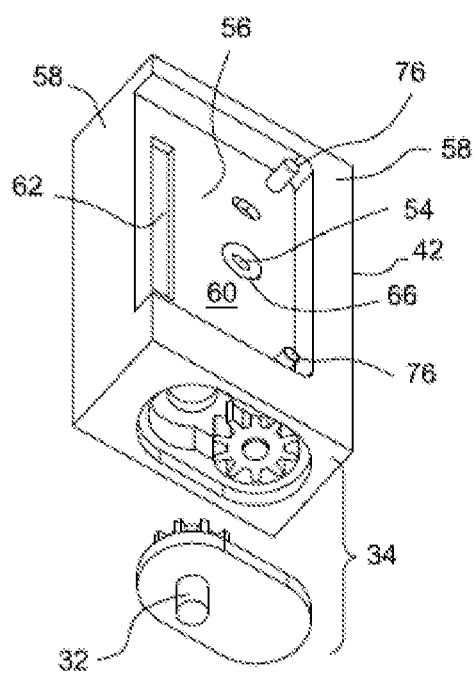

FIG. 7 is another perspective view of the hollow main body of the cartridge.

Figure 8:
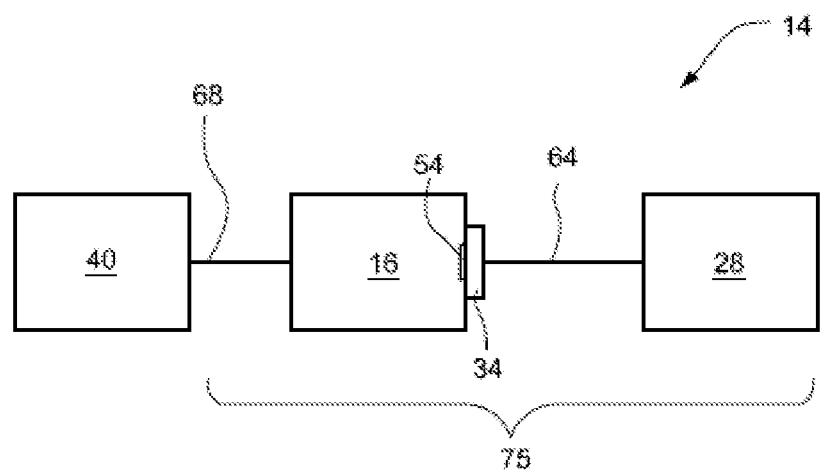

FIG. 8 is a schematic diagram of the cartridge of FIG. 1.

Figure 9:
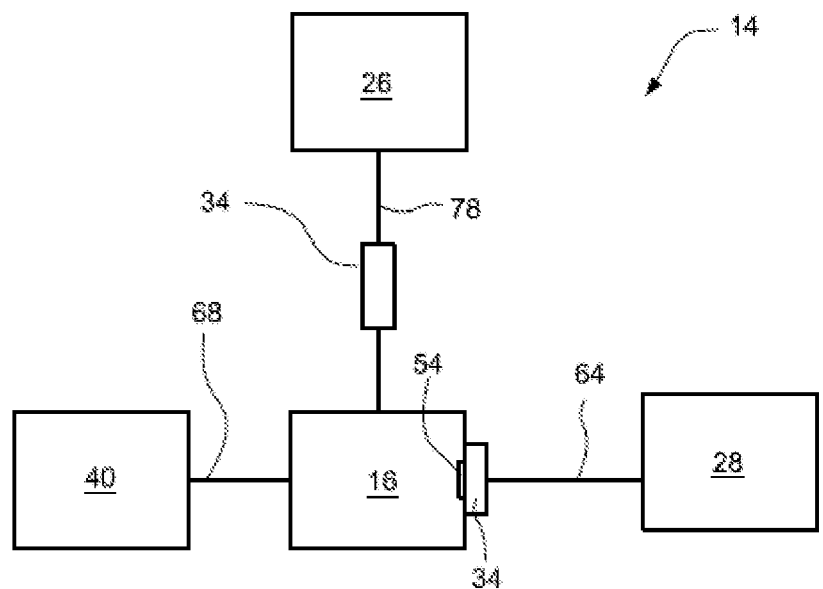

FIG. 9 is a schematic diagram of an alternate cartridge.

MODE FOR THE INVENTION

Mode for Invention

FIG. 1 shows microvaporizer 10 for generating an aerosol for inhalation by a user.

The microvaporizer 10 may be configured as a vaping device for delivery of a nicotine vapor to the mouth of a user. The microvaporizer 10 may also be configured to deliver a medicinal vapor, such as an aerosol infused with asthma drugs, to the mouth of a user. Moreover, the microvaporizer may be configured for use to deliver other types of vapor (aerosols) to a user.

The microvaporizer 10 may include a base 12, a cartridge 14 and a flat panel heater 16. The base 12 may be a hollow handheld device. The outer surfaces of the base 12 may be shaped to be easily held in one hand and carried in a user's pocket or purse.

The base 12 may house a battery 18, electronic circuits 20 and electrical conductors 22 connecting the battery 18, electronic circuits 20 and the flat panel heater 16. The electronic circuits 20 may control delivery of electrical power from the battery 18 to resistive heating elements 24, e.g, conductive loops, in the flat panel heater 16.

The base 12 may also house a secondary reservoir 26 which may provide fluid to the cartridge 14. The secondary reservoir 26 may be internal to the base 12 and may be behind a mount (not shown) for the cartridge 14. The secondary reservoir 26 may be optional. It is contemplated that the secondary reservoir 26 may be in addition to a primary reservoir 28 in the cartridge 14 if the primary reservoir 28, e.g, fluid conduit, is too small to store enough fluid to generate vapor for an extended period, such as several days. It is further contemplated that the primary reservoir 28 may be omitted and the secondary reservoir 26 in the base 12 may be the only reservoir in the microvaporizer 10.

The base 12 may also include a motor 30 to drive a drive shaft 32 of a pump 34 in the cartridge 14. The pump 34 may pump fluid from the cartridge 14 into and through the flat panel heater 16 and/or pump fluid from the secondary reservoir 26 into the primary reservoir 28. It is contemplated that the pump 34 may pump fluid from the secondary reservoir 26 into the primary reservoir 28 once a certain period of time, e.g., 20 to 120 seconds, has elapsed since the last inhaling action by the user. It is contemplated that the pump 34 may pump unused fluid from the flat panel heater 16 into the primary reservoir 28 and/or the secondary reservoir 26.

The cartridge 14 may be mounted in or on the base 12. The base 12 may have a slot to receive the cartridge 14 or may have a sidewall with a recess to receive and hold the cartridge 14. The cartridge 14 may be permanently attached to the base 12 or may be removable from the base 12.

Electrical connectors 36 that receive tabs 38 on the flat panel heater 16 may be internal to the housing of the base 12. The electrical connectors 36 may provide a conductive coupling between the electrical conductors 36 internal to the base 12 and the resistive heating elements 24 of the flat panel heater 16.

As illustrated in FIGS. 1 to 4, the cartridge 14 may include a user interface (e.g., a mouthpiece) 40 for delivering the aerosol directly to the user's airways. The user interface 40 may be permanently attached to the cartridge 14 or may be removable from the cartridge 14. The cartridge 14 may also have a universal connection so that more than one size or type of user interface 40 may be attached to the cartridge 14.

The cartridge 14 may also include a hollow main body 42 which houses the primary reservoir 28, at least a part of the pump 34 and a mounting structure 44 to receive the flat panel heater 16. The primary reservoir 28 may have liquid capacity of in a range of one to thirty milliliter capacity, such as, for example, a two milliliter capacity.

The dimensions of the cartridge 14 may be sufficiently small to fit in the handheld base 12. For example, the cartridge 14 may have a generally rectangular shape, not including the connection to the user interface 40 or the drive shaft 32 of the pump 34. The rectangular shape may have a length in a range of 1 to 2 inches (2.5 cm to 5 cm), a width of 0.5 to 1 inch (1.3 to 1 cm) and a thickness of 0.25 to 0.5 inch (0.6 to 1.3 cm).

The flat panel heater 16 may be a flat panel assembly of a metallic layer (the resistive heating elements 24) that is sandwiched between non-conductive substrate plates 46, 48. As shown in FIGS. 1, 3 and 4, the substrate plates 46, 48 may be transparent to show the resistive heating elements 24. The transparency of the substrate plates 46, 48 may facilitate a visual inspection of the operation of the flat panel heater 16. The substrates 46, 48 may be flat panels formed of plastic or other material which may be non-conductive or a dielectric. The resistance heating elements 24 may be made of a thin layer of electrically conducting material, while the substrates 46, 48 may be made of electrically insulating material. Narrow gaps in the metallic layer may form channels 52 with the substrates 46, 48. The electrically conducting material surrounding the gaps may heat, vaporize and transform the chemically infused fluid into an aerosol. The metallic layer may include the tabs 38 and heating elements 50 that are part of a conductive circuit formed by the metallic layer 24. Current may flow through the tabs 38 and the heating elements 50, e.g., loops, to heat the heating elements 50 and thereby vaporize the fluid contained within in the loops or otherwise at the heating elements 50. In addition, the metallic layer 24 may include the channels 52 through which the fluid may flow to the heating elements 50. The metallic layer 24 need not be entirely metallic and may be non-conductive with conductive paths between the tabs 38 and heating elements 50.

Further, the channels 52 may be etched into a side surface of one or both of the substrate plates 46, 48 and the conductive paths from the tabs 38 to and including the heating elements 50 may be embedded in the side surface of the substrate plate(s) 46, 48. In this configuration, a metallic layer may not be needed.

An inlet opening (not shown) in one of the substrates 46, 48 may function as an inlet of the flat panel heater 16 and may align with a fluid port 54 in the mounting structure 44 in the cartridge 14 when the flat panel heater 16 is mounted in the recess 56. The fluid port 54 may comprises the first fluid opening in the recessed planar wall 60 and may allow fluid to flow from the primary reservoir 26 in the cartridge 14, through the fluid port 54 and the inlet opening in said one of the substrates 46, 38 and into the channels 52 of the flat panel heater 16.

The mounting structure 44 for the flat panel heater 16 may include a recess 56 in a side wall of the hollow main body 42 of the cartridge 14. The recess 56 may be deep enough so that the outermost substrate plate 48 of the flat panel heater 16 may be flush with an outer surface 58 of the hollow main body 42. The shape of the perimeter of the recess 56 may be complimentary to the shape of the perimeter of the flat panel heater 16 to facilitate a tight fit between the flat panel heater 16 and the hollow main body 42. The perimeter may be defined by a ledge between the recess 56 and the outer surface 58. The recess 56 may be open on one side to receive the flat panel heater 16. A recessed planar wall 60 against which the flat panel heater 16 may be mounted against may be located opposite the recess opening. The recessed planar wall 60 may include the fluid port 54 and a discharge port 62.

The fluid port 54 may be fluidly connected to the primary reservoir 28 either directly or by way of a fluid passage 64 internal to the cartridge 14. In addition, the fluid port 54 may sealingly connect to an inlet of the flat panel heater 16 (i.e., the inlet opening in one of said substrates 46, 48) when the flat panel heater 16 is mounted in the recess 56. A seal, e.g., an O-ring, 66 may be fixed to the fluid port 54 to ensure a sealed connection with the inlet of the flat panel heater 16. Alternatively, the seal 66 may be fixed to the inlet of the flat panel heater 16.

As shown in FIGS. 5-7, the pump 34 may be include a screw valve (e.g., opposing gears). As shown schematically in FIG. 8, the pump 34 may pump the liquid from the primary reservoir 28 into and out of the flat panel heater 16 by creating a pressure difference across the channels 52 in the flat panel heater 16. Alternatively or in addition to, a secondary pump (not shown) may also be used to pump fluid into and out of the primary reservoir 28 in the cartridge 14 from the secondary reservoir 26 in the base 12. It is contemplated that other types of pumps may be used (e.g., piston pumps, gear pumps, diaphragm pumps, etc.).

The discharge port 62 (comprising the second fluid opening in the recessed planar wall 60) may be fluidly connected to the user interface 40 or a connection to the user interface 40 by way of a vapor passage 68 between an outlet of the flat panel heater 16 and the user interface 40. The heating elements 50 of the flat panel heater 16 may convert the fluid to vapor. The vapor may flow from the heating elements 50 through the outlet of the flat panel heater 16 (i.e., the vapor openings 70, e.g., slots, in one of the substrates 46, 48 that faces the recessed planar wall 60 of the recess 56 in the cartridge 14). The discharge port 62 in the recessed planar wall 60 may also be considered a vapor inlet, e.g., a slot or opening, that is aligned with the vapor opening(s) 70 of the flat panel heater 16. Vapor formed at the heating elements 50 may flow through the vapor opening(s) 70, into the vapor inlet (or discharge port 62 in the recess 56 of the cartridge 14 and through the vapor passage 68 in the cartridge 14 to the user interface 40.

It is contemplated that the primary reservoir 28, the fluid passage 64, the fluid port 54, the flat panel heater 16 and the vapor passage 68 may together form a fluid flow path 75. Accordingly, mounting the flat panel heater 16 in the recess 56 of the cartridge 14 may complete or fill a gap in the fluid flow path 75 and may fluidly connect the fluid port 54 to the discharge port 62. Conversely, removing the flat panel heater 16 from the recess may leave a gap in the fluid flow path 75. It is contemplated that one or more of the secondary reservoir 26, the user interface 40, and the pump 34 may optionally be part of the fluid flow path 75.

To mount the flat panel heater 16 in the recess 56 of the cartridge 14, a flat outer side of one of the substrates 46, 48 may be pressed or slid into the recess 56. Holes 74 in the flat panel heater may receive protrusions (e.g., posts) 76, extending out from the recessed planar wall 60.

The holes 74 may be positioned outside of the fluid flow path 75. An interference fit between the holes 74 in the flat panel heater and the posts 76 of the cartridge 14 may secure the flat panel heater 16 to the cartridge 14. It is contemplated that the protrusions 76 may extend from the flat panel heater 16 and that the recessed planar wall 60 may include the holes 74. Alternatively or in addition, the flat panel heater 16 may be secured to the cartridge 14 with a clip, snap-fit or other fastening system.

It is contemplated that the cartridge 14 may be capable of vaporizing two different flows of fluid simultaneously. In this configuration, the hollow main body 42 may include the fluid passage 64 and a second fluid passage 78 between the pump 34 and the fluid port 54. This configuration may also include a second pump 34 that operates in parallel with the first pump 34. For example, the first pump 34 may pump a first fluid through the fluid passage 64, while at the same time, the second pump 34 may pump a second fluid through the second fluid passage 78. It is contemplated that the primary reservoir 28 may contain the first fluid, while the secondary reservoir 26 may contain the second fluid. Alternatively, both fluids may be stored within the hollow main body 42. Also, it is further contemplated that only the second fluid passage 78 may be omitted and both fluids may be combined upstream of the flat panel heater 16. It is also contemplated that both fluids may be stored in the same reservoir. It should be understood that in the configuration including the second pump 34 and the second fluid passage 78, both the second pump 34 and the second fluid passage 78 may be part of the fluid flow path 75.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise.

The invention claimed is:

1. A cartridge configured to be mounted to a microvaporizer device, the cartridge comprising:
    a hollow main body with a recessed wall;
    a reservoir inside the hollow main body that is configured to retain a body of liquid;
    a flat panel heater adjacent the recessed wall, the flat panel heater being configured to vaporize liquid from the reservoir;
    a mouthpiece at one end of the hollow main body, the mouthpiece comprising an opening configured to discharge the vapor generated by the flat panel heater to a user; and
    a vapor passage inside the hollow main body that is configured to convey the vapor generated by the flat panel heater to the mouthpiece,
    wherein both the reservoir and the vapor passage extend to the same end of the hollow main body as the mouthpiece,
    wherein the reservoir is separated from the vapor passage by an interior wall inside the hollow main body,
    wherein the recessed wall comprises two fluid openings configured to fluidly connect to fluid passages in the flat panel heater,
    wherein a first one of the fluid openings in the recessed wall is fluidly connected to an inlet of the flat panel heater so that the flat panel heater receives fluid through the first fluid opening in the recessed wall, and
    wherein a second one of the fluid openings in the recessed wall is fluidly connected to an outlet of the flat panel heater so that fluid vaporized by the flat panel heater is discharged through the second fluid opening of the recessed wall.

2. The cartridge of claim 1, wherein at least one of the two fluid openings comprises a seal.

3. The cartridge of claim 2, wherein the seal is an O-ring.

4. The cartridge of claim 1, wherein the recessed wall further comprises a mounting structure configured to engage the flat panel heater to align the flat panel heater within the recess in the hollow main body.

5. The cartridge of claim 4, wherein the mounting structure comprises a pair of protrusions configured to engage a respective pair of alignment openings in the flat panel heater.

6. The cartridge of claim 1, wherein the hollow main body comprises a universal connection adapted to connect to more than one type of mouthpiece.

7. A microvaporizer device configured to deliver an aerosol to a user's airways, the microvaporizer device comprising:
    a power supply; and
    the cartridge of claim 1.

8. The microvaporizer device of claim 7, further comprising a base containing the power supply and electronic circuits configured to control the flat panel heater.

9. The microvaporizer device of claim 8, wherein the cartridge is removably connected to the base.

10. The microvaporizer device of claim 8, wherein the base further contains a secondary reservoir configured to supply liquid to the cartridge.

11. A cartridge configured to be mounted to a microvaporizer device, the cartridge comprising:
    a vapor passage configured to deliver aerosol to a user interface;
    a hollow main body with a recess;
    a storage tank configured to retain a chemically infused liquid, the storage tank being contained inside the hollow main body; and
    a flat panel heater mounted to a recessed wall in the recess of the hollow main body, the flat panel heater being a unitary component configured so that positioning the flat panel heater in the recess fluidly connects the flat panel heater to the storage tank and the user interface,
    wherein the recessed wall comprises two fluid openings configured to fluidly connect to fluid passages in the flat panel heater,
    wherein a first one of the fluid openings in the recessed wall is fluidly connected to an inlet of the flat panel heater so that the flat panel heater receives fluid through the first fluid opening in the recessed wall, and
    wherein a second one of the fluid openings in the recessed wall is fluidly connected to an outlet of the flat panel heater so that fluid vaporized by the flat panel heater is discharged through the second fluid opening of the recessed wall.

12. The cartridge of claim 11, wherein the flat panel heater is configured so that an outer surface of the flat panel heater is flush with an outer surface of the cartridge when the flat panel heater is positioned in the recess.

13. The cartridge of claim 11, wherein the flat panel heater is configured to be retained in the recess by friction.

14. The cartridge of claim 11, further comprising a pump configured to pump liquid in and out of the storage tank.

15. The cartridge of claim 14, wherein the pump is configured to pump the liquid in and out of the flat panel heater.

16. The cartridge of claim 14, wherein the pump is configured to be actuated at predetermined intervals of time.

* * * * *